(12) United States Patent
Masse

(10) Patent No.: US 7,985,750 B2
(45) Date of Patent: Jul. 26, 2011

(54) SUBSTITUTED OXAZOLIDINONE DERIVATIVES

(75) Inventor: Craig E. Masse, Cambridge, MA (US)

(73) Assignee: Concert Pharmaceuticals, Inc., Lexington, MA (US)

(*) Notice: Subject to any disclaimer, the term of this patent is extended or adjusted under 35 U.S.C. 154(b) by 114 days.

(21) Appl. No.: 12/228,662

(22) Filed: Aug. 14, 2008

(65) Prior Publication Data

US 2009/0137535 A1    May 28, 2009

Related U.S. Application Data

(60) Provisional application No. 60/964,693, filed on Aug. 14, 2007.

(51) Int. Cl.
*A61K 31/535* (2006.01)
*C07D 413/14* (2006.01)

(52) U.S. Cl. .................... 514/236.8; 544/137

(58) Field of Classification Search .............. 548/137; 514/236.8; 544/137
See application file for complete search history.

(56) References Cited

U.S. PATENT DOCUMENTS

| | | | |
|---|---|---|---|
| 6,221,335 B1 | 4/2001 | Foster | |
| 6,440,710 B1 | 8/2002 | Keinan et al. | |
| 6,603,008 B1 | 8/2003 | Ando et al. | |
| 7,517,990 B2 | 4/2009 | Ito et al. | |
| 2004/0242660 A1 | 12/2004 | Straub et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |
| 2009/0076264 A1 | 3/2009 | Czarnik | |

FOREIGN PATENT DOCUMENTS

| | | |
|---|---|---|
| DE | 10 2004 062 475 A1 | 7/2006 |
| DE | 10 2005 047 564 A1 | 5/2007 |
| EP | 1 479 675 A1 | 11/2004 |
| WO | WO 95/26325 | 10/1995 |
| WO | WO 2007/118651 A1 | 10/2007 |

OTHER PUBLICATIONS

Roehrig et al., J. Med. Chem., 2005, 48, 5900-5908.*
Baillie, Pharmacology Rev.1981; 33: 81-132.*
PCT International Search Report for International Application No. PCT/US2008/009704, Date of Mailing: Dec. 23, 2008.
PCT Written Opinion of the International Searching Authority for International Application No. PCT/US2008/009704, Date of Mailing: Dec. 23, 2008.
Fisher, M.B. et al., "The Complexities Inherent in Attempts to Decrease Drug Clearance by Blocking Sites of CYP-Mediated Metabolism," Curr. Opin. Drug Discov., 9(1): 101-109 (Jan. 2006).

Kushner, D.J. et al., "Pharmacological Uses and Perspectives of Heavy Water and Deuterated Compounds," Can. J. Physiol. Pharmacol., 77(2): 79-88 (Feb. 1999).
Weinz, C. et al., "195. In Vitro Metabolism of Bay 59-7939—An Oral, Direct Factor Xa Inhibitor" and "196. Metabolism and Distribution of [14C]Bay 59-7939—An Oral, Direct Factor Xa Inhibitor—In Rat, Dog and Human," Drug Metabolism Reviews, vol. 36, Issue Suppl. 1, p. 98 (Dec. 2004).
Baillie, Thomas A., "The Use of Stable Isotopes in Pharmacological Research", Pharmacological Reviews, vol. 33, No. 2, pp. 81-132, 1981.
Browne, Thomas R., "Stable Isotope Techniques in Early Drug Development: An Economic Evaluation", J. Clin. Pharmacol, vol. 38, pp. 213-220, 1998.
Cherrah, et al., "Study of Deuterium Isotope Effects on Protein Binding by Gas Chromatography/Mass Spectrometry, Caffeine and Deuterated Isotopomers", Biomedical and Environmental Mass Spectrometry, vol. 14, pp. 653-657, 1987.
Dyck, et al., "Effects of Deuterium Substitution on the Catabolism of β-Phenylethylamine: An In Vivo Study", Journal of Neurochemistry, vol. 46, No. 2, pp. 399-404, 1986.
Foster, Allan B., "Deuterium isotope effects in studies of drug metabolism", TIPS, pp. 524-527, 1984.
Foster, Allan B., "Deuterium Isotope Effects in the Metabolism of Drugs and Xenobiotics: Implications for Drug Design", Advances in Drug Research, vol. 14, pp. 1-40, 1985.
Gouyette, et al., "Synthesis of Deuterium-labelled Elliptinium and its Use in Metabolic Studies", Biomedical and Environmental Mass Spectrometry, vol. 15, pp. 243-247, 1988.
Haskins, N.J., "The Application of Stable Isotopes in Biomedical Research", Biomedical Mass Spectrometry, vol. 9, No. 7, pp. 269-277, 1982.
Honma, et al., "Liberation of Deuterium from the Piperidine Ring during Hydroxylation", Drug Metabolism and Disposition, vol. 15, No. 4, pp. 551-559, 1987.
Pieniaszek, et al., "Moricizine Bioavailablity via Simultaneous, Dual, Stable Isotope Administration: Bioequivalence implications", The Journal of Clinical Pharmacology, vol. 39, pp. 817-825, 1999.
Tonn, et al., "Simultaneous Analysis of Diphenhydramine and a Stable Isotope Analog ($^{2}H_{10}$)Diphenhydramine Using Capillary Gas Chromatography with Mass Selective Detection in Biological Fluids from Chronically Instrumented Pregnant Ewes", Biological Mass Spectrometry, vol. 22, pp. 633-642, 1993.
Wolen, Robert L., "The Application of Stable Isotopes to Studies of Drug Bioabailablity and Bioequivalence", The Journal of Clinical Pharmacology, vol. 26, pp. 419-424, 1986.

* cited by examiner

Primary Examiner — Rebecca L Anderson
(74) Attorney, Agent, or Firm — McCarter & English LLP; Steven G. Davis

(57) ABSTRACT

This invention relates to novel compounds that are substituted oxazolidinones derivatives and pharmaceutically acceptable salts thereof. More specifically, this invention relates to novel oxazolidinones compounds that are derivatives of rivaroxaban. The invention also provides pyrogen-free compositions comprising one or more compounds of the invention and a carrier, and the use of the disclosed compounds and compositions in methods of treating diseases and condition that are beneficially treated by administering a selective inhibitor of factor Xa, such as rivaroxaban.

6 Claims, No Drawings

SUBSTITUTED OXAZOLIDINONE DERIVATIVES

RELATED APPLICATION

This application claims the benefit of U.S. Provisional Application No. 60/964,693, filed on Aug. 14, 2007. The entire teachings of the above application is incorporated herein by reference.

BACKGROUND OF THE INVENTION

Rivaroxaban, also known as 5-chloro-N-[2-oxo-3-[4-(3-oxomorpholin-4-yl)phenyl]oxazolidin-5(S)-ylmethyl]thiophene-2-carboxamide, acts by inhibition of the active form of coagulation factor Xa.

Rivaroxaban is currently in clinical trials for pulmonary embolism, stroke, thromboembolism, deep venous thrombosis, thrombosis, and acute coronary syndrome (http://clinicaltrials.gov/).

Rivaroxaban is converted to two major metabolites in vivo, the CYP3A4 mediated product of morpholinone ring oxidation (M1), and the product of chlorothiophenyl amide hydrolysis and subsequent glycine conjugation (M4). Neither metabolite is active. (Weinz, C et al., Drug Metab Rev, 2004, 36 (suppl 1): 98).

Adverse events associated with the use of rivaroxaban include, but are not limited to, ageusia (loss of taste), ecchymosis (bruising) and headache (Kubitza, D et al., Cl Pharmacol Therapeutics, 2005, 78 (4): 412-421).

Despite the beneficial activities of rivaroxaban, there is a continuing need for new compounds for treating the aforementioned diseases and conditions.

SUMMARY OF THE INVENTION

This invention relates to novel compounds that are substituted oxazolidinones derivatives and pharmaceutically acceptable salts thereof. More specifically, this invention relates to novel oxazolidinones compounds that are derivatives of rivaroxaban. The invention also provides pyrogen-free compositions comprising one or more compounds of the invention and a carrier, and the use of the disclosed compounds and compositions in methods of treating diseases and condition that are beneficially treated by administering a selective inhibitor of factor Xa, such as rivaroxaban.

The compounds of the invention are represented by Formula I:

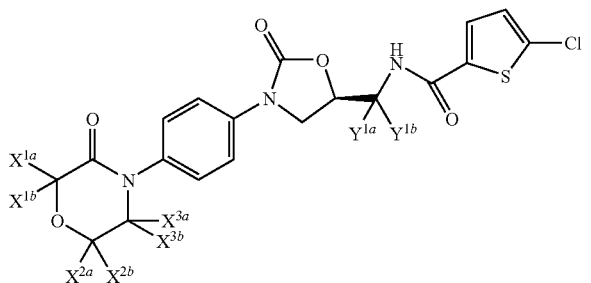

I or a pharmaceutically acceptable salt thereof, wherein:
each of $X^{1a}$, $X^{1b}$, $X^{2a}$, $X^{2b}$, $X^{3a}$, $X^{3b}$, $Y^{1a}$, and $Y^{1b}$ are independently selected from hydrogen and deuterium, and at least one X or one Y variable is deuterium.

The compounds, pharmaceutically acceptable salts thereof and compositions of the invention, are useful for treating diseases that are effectively treated by a compound which inhibits coagulation factor Xa, such as rivaroxaban. As such the present invention includes methods of treating a disease which is susceptible to treatment by a compound which inhibits coagulation factor Xa, such a rivaroxaban, comprising administering to a patient in need thereof an effective amount of: (i) a compound or pharmaceutically acceptable salt thereof; or (ii) a pyrogen-free composition (e.g., a pharmaceutical composition), described herein.

Diseases and conditions susceptible to treatment with a compound which inhibits coagulation factor Xa, such as rivaroxaban, include but are not limited to pulmonary embolism, stroke, thromboembolism, deep venous thrombosis, thrombosis, acute coronary syndrome, disorders of coagulation, microangiopathy and associated disorders such as thrombocytopenic purpura.

The compounds and compositions of the invention are also useful as reagents in methods for determining the concentration of rivaroxaban in solution, examining the metabolism of rivaroxaban and other analytical studies. An additional utility of compounds of any of the formulae herein include their use as internal standards to determine the true concentrations of rivaroxaban in biological matrices, such as plasma.

DETAILED DESCRIPTION OF THE INVENTION

The terms "ameliorate" and "treat" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of rivaroxaban will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Ganes L Z et al., Comp Biochem Physiol Mol Integr Physiol 1998, 119:725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3340 (50.1% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopologue" refers to a species that differs from a specific compound of this invention only in the isotopic composition thereof.

The term "compound," when referring to compounds of the invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues will be less than 49.9% of the compound. The term "compound," as used herein, is also intended to include any salts, solvates or hydrates thereof.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert", "*t*" and "t-" each refer to tertiary. "U.S." refers to the United States of America.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula I:

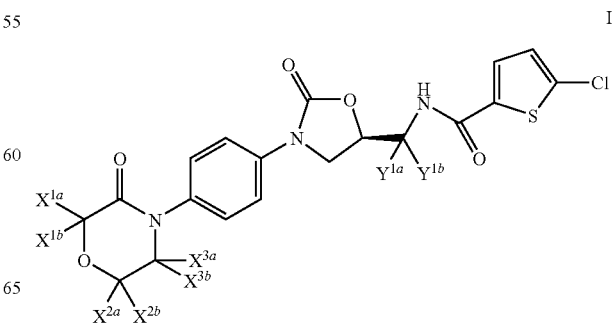

I or a pharmaceutically acceptable salt thereof, wherein:
each of $X^{1a}$, $X^{1b}$, $X^{2a}$, $X^{2b}$, $X^{3a}$, $X^{3b}$, $Y^{1a}$, and $Y^{1b}$ are independently selected from hydrogen and deuterium, and at least one X or one Y variable is deuterium.

Other embodiments of Formula I include the following.

a) A compound where each X and each Y bound to a common carbon atom is the same.

b) A compound where $X^{1a}$ and $X^{1b}$ are simultaneously deuterium.

c) A compound where $X^{2a}$ and $X^{2b}$ are simultaneously deuterium.

d) A compound where $X^{3a}$ and $X^{3b}$ are simultaneously deuterium.

e) A compound where $X^{1a}$, $X^{1b}$, $X^{2a}$ and $X^{2b}$ are simultaneously deuterium, and $X^{3a}$ and $X^{3b}$ are simultaneously hydrogen. In one aspect of this embodiment, each Y variable is hydrogen. In another aspect, each Y variable is deuterium.

f) A compound where $X^{1a}$, $X^{1b}$, $X^{2a}$ and $X^{2b}$ are simultaneously hydrogen, and $X^{3a}$ and $X^{3b}$ are simultaneously deuterium. In one aspect of this embodiment, each Y variable is hydrogen. In another aspect, each Y variable is deuterium.

g) A compound where $X^{1a}$, $X^{1b}$, $X^{3a}$ and $X^{3b}$ are simultaneously deuterium, and $X^{2a}$ and $X^{2b}$ are simultaneously hydrogen. In one aspect of this embodiment, each Y variable is hydrogen. In another aspect, each Y variable is deuterium.

h) A compound where $X^{1a}$, $X^{1b}$, $X^{3a}$ and $X^{3b}$ are simultaneously hydrogen, and $X^{2a}$ and $X^{2b}$ are simultaneously deuterium. In one aspect of this embodiment, each Y variable is hydrogen. In another aspect, each Y variable is deuterium.

i) A compound where $X^{2a}$, $X^{2b}$, $X^{3a}$ and $X^{3b}$ are simultaneously deuterium, and $X^{1a}$ and $X^{1b}$ are simultaneously hydrogen. In one aspect of this embodiment, each Y variable is hydrogen. In another aspect, each Y variable is deuterium.

j) A compound where $X^{2a}$, $X^{2b}$, $X^{3a}$ and $X^{3b}$ are simultaneously hydrogen, and $X^{1a}$ and $X^{1b}$ are simultaneously deuterium. In one aspect of this embodiment, each Y variable is hydrogen. In another aspect, each Y variable is deuterium.

k) A compound where $X^{1a}$, $X^{1b}$, $X^{2a}$, $X^{2b}$, $X^{3a}$ and $X^{3b}$ are simultaneously deuterium. In one aspect of this embodiment, each Y variable is hydrogen. In another aspect, each Y variable is deuterium.

l) A compound where $Y^{1a}$ and $Y^{1b}$ are simultaneously deuterium.

Examples of specific compounds of Formula I are shown in Table 1 below.

TABLE 1

| Examples of Compounds of Formula I | | | | | | | | |
|---|---|---|---|---|---|---|---|---|
| Compound | $X^{1a}$ | $X^{1b}$ | $X^{2a}$ | $X^{2b}$ | $X^{3a}$ | $X^{3b}$ | $Y^{1a}$ | $Y^{1b}$ |
| 100 | D | D | D | D | D | D | D | D |
| 101 | D | D | D | D | D | D | H | H |
| 102 | H | H | H | H | H | H | D | D |
| 103 | D | D | D | D | H | H | H | H |
| 104 | D | D | D | D | H | H | D | D |
| 105 | D | D | H | H | D | D | H | H |
| 106 | D | D | H | H | D | D | D | D |
| 107 | H | H | D | D | D | D | H | H |
| 108 | H | H | D | D | D | D | D | D |
| 109 | D | D | H | H | H | H | D | D |
| 110 | H | H | D | D | H | H | D | D |
| 111 | H | H | H | H | D | D | D | D |
| 112 | D | D | H | H | H | H | H | H |
| 113 | H | H | D | D | H | H | H | H |
| 114 | H | H | H | H | D | D | H | H |

In another set of embodiments, any atom not designated as deuterium in any of the embodiments set forth above is present at its natural isotopic abundance.

The synthesis of compounds of Formula I can be readily achieved by synthetic chemists of ordinary skill. Relevant procedures and intermediates are disclosed, for instance in PCT Publications WO 03/000256 and WO 2005/068456A1; EPO publication EP 1479675; and in Roehrig, S et al., J Med Chem 2005, 48:5900.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

Exemplary Synthesis

Compounds of this invention may be prepared according to the schemes described below.

Scheme 1. Synthesis of a Compound of Formula I.

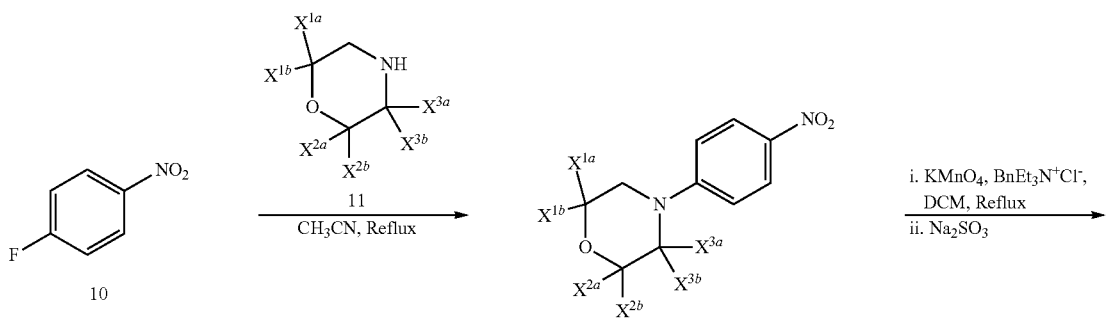

-continued
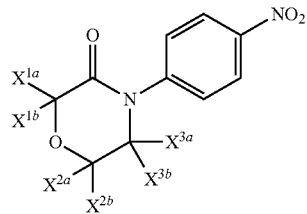 13
H₂, Pd/C → 14
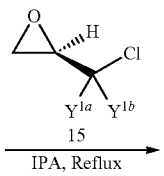 15
IPA, Reflux →
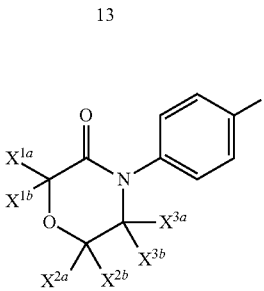 16
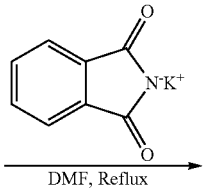
DMF, Reflux →
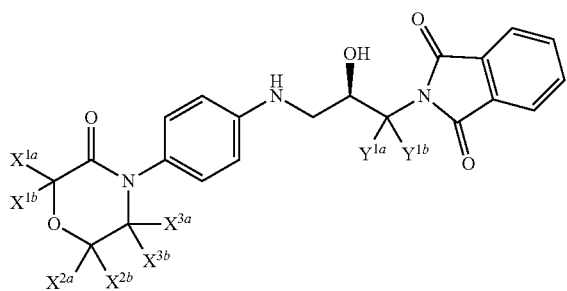 17
1. CDI, DCM
2. NH₂NH₂, MeOH
   Reflux
→
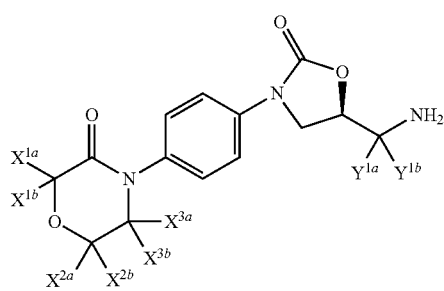 18
Pyridine, THF →
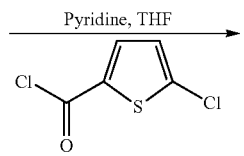
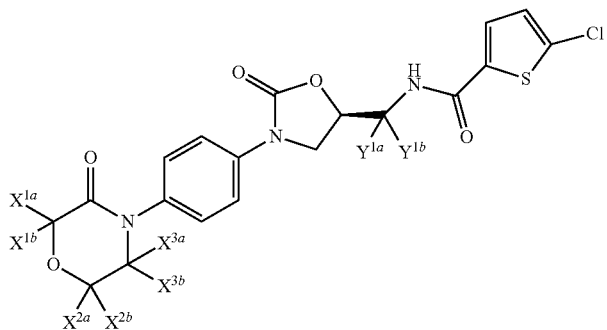
Formula I Scheme 1 above shows a general route for making compounds of Formula I. Commercially available morpholine and 2,2,3,3,5,5,6,6-$d_8$ morpholine may be used interchangeably as reagent 11 to prepare 1-nitro-4-morpholinobenzene intermediate 12 from 1-nitro-4-fluorobenzene (10). The perdeuteromorpholine reagent 11 results in a compound of Formula I wherein $X^{1a}$, $X^{1b}$, $X^{2a}$, $X^{2b}$, $X^{3a}$ and $X^{3b}$ are simultaneously deuterium. Alternatively, 2,2,6,6-$d_4$-morpholine or 3,3,5,5-$d_4$-morpholine may be used as reagent 11.

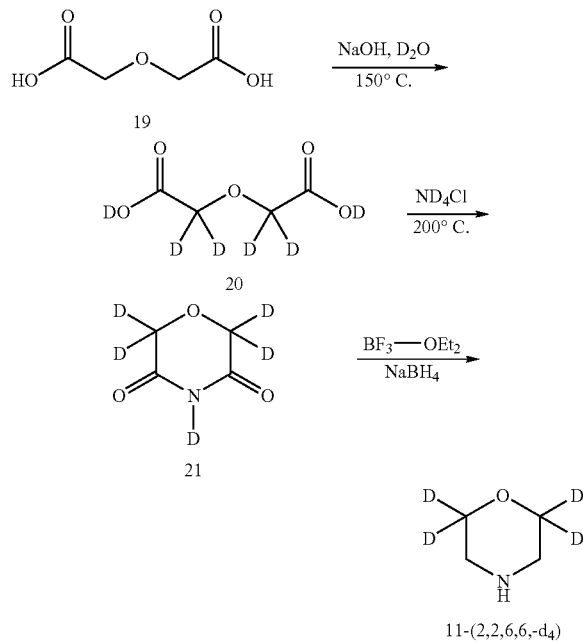

Scheme 2 Synthesis of 2,6,6-$d_4$-morpholine.

Scheme 2 shows a route for preparing 2,6,6-$d_4$-morpholine 11-(2,2,6,6-$d_4$). Treatment of commercially available diglycolic acid (19) with sodium hydroxide in deuterated water according to the procedure described by Cam, P L et al., Chemica Scripta 1971, 1:65-68 affords the diglycolate 20. Condensation with commercially available ammonium chloride-$d_4$ with heating affords the $d_5$-diglycolimide 21. Reduction of the imide 21 with in-situ generated diborane affords 11-(2,2,6,6-$d_4$). The use of 2,2,6,6-$d_4$-morpholine as reagent 11 in Scheme 1 provides a compound of Formula I wherein $X^{1a}$, $X^{1b}$, $X^{2a}$ and $X^{2b}$ are simultaneously deuterium, and $X^{3a}$ and $X^{3b}$ are simultaneously hydrogen.

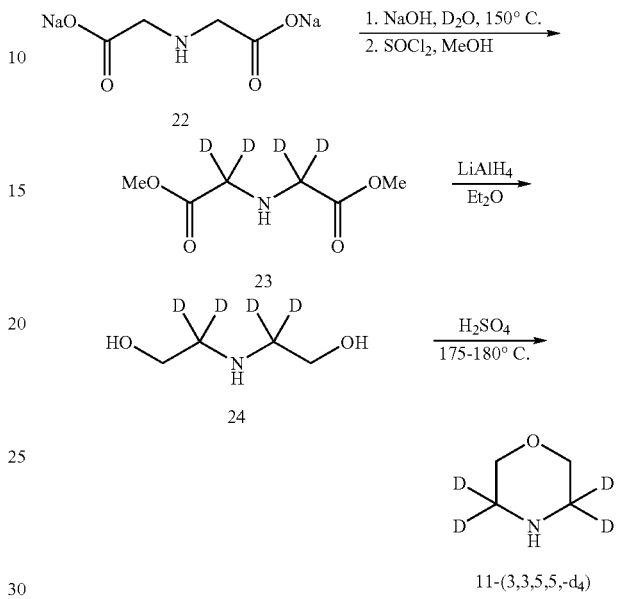

Scheme 3A. Synthesis of 3,3,5,5-$d_4$-morpholine.

Scheme 3 shows a route for preparing 3,3,5,5-$d_4$-morpholine 11-(3,3,5,5-$d_4$). Treatment of commercially available disodium iminodiacetate (22) with sodium hydroxide in deuterated water ($D_2O$), followed by treatment with dry methanol and thionyl chloride utilizing the procedure described by Cam, P L et al., Chemica Scripta 1971, 1:65-68, affords tetradeuterated dimethylester 23. Subsequent reduction of the diester with lithium aluminum hydride affords $d_4$-diethanolamine 24. The final step involves an acid-catalyzed thermal cyclization to give 3,3,5,5-$d_4$-morpholine 11-(3,3,5,5-$d_4$). The use of 3,3,5,5-$d_4$-morpholine as reagent 11 in Scheme 1 produces a compound of Formula I wherein $X^{1a}$, $X^{1b}$, $X^{2a}$ and $X^{2b}$ are simultaneously hydrogen, and $X^{3a}$ and $X^{3b}$ are simultaneously deuterium.

Scheme 3B. Alternative Synthesis of 3,3,5,5-$d_4$-morpholine

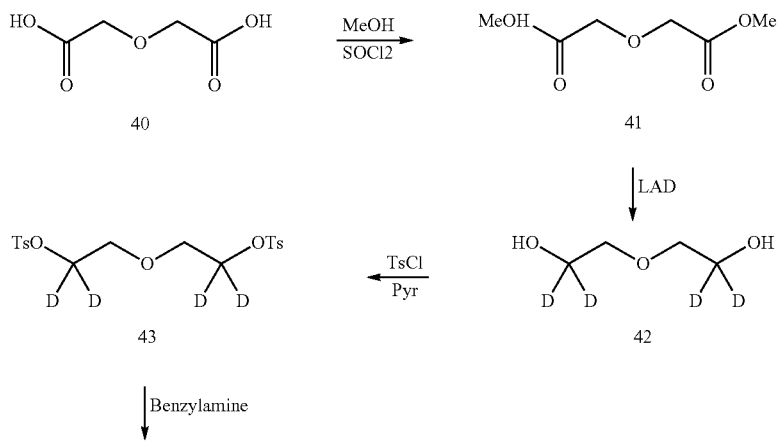

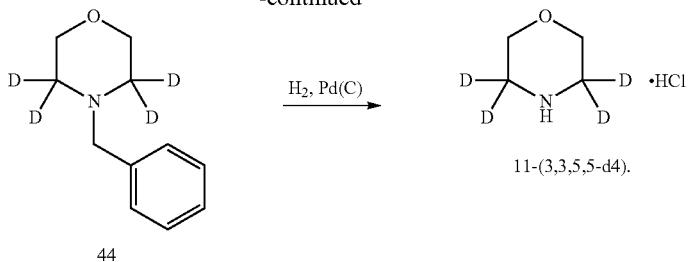

An alternative synthesis of 3,3,5,5-$d_4$-morpholine is depicted in Scheme 3B. Thus, diglycolic acid 40 is converted the corresponding diester 41 using thionyl chloride in methanol. LAD reduction of diester 41 provides deuterated 2,2'-oxydiethanol 42, which is converted to the corresponding ditosylate 43 under conventional conditions using tosyl chloride and pyridine. Treatment of ditosylate 43 with benzylamine provides N-benzyl-morpholine 44, which is deprotected under hydrogenolysis conditions to provide the desired 3,3,5,5-$d_4$-morpholine 11-(3,3,5,5-$d_4$).

Additional compounds of Formula I are synthesized by using alternate routes for preparing deuterated forms of intermediate 13 as shown in the schemes below. These intermediates are useful in subsequent steps set forth in Scheme 1.

Scheme 4. Synthesis of to 4-(4-nitrophenyl)-6,6-$d_2$-morpholin-3-one.

Scheme 4 above shows a route to 4-(4-nitrophenyl)-6,6-$d_2$-morpholin-3-one (13). Treatment of commercially available methyl chloroacetate (24) with 1,1-$d_2$-2-chloroethanol 25 (prepared using the protocol described by McManus, S P et al., J Org Chem 1993, 58:6466-6469) in the presence of sodium hydride according to the procedure described by Maruyama, T et al., Bioorg Med Chem 2002, 10:975-988 affords dideuterated methylester 26. Saponification of the methyl ester 26 and exposure of the resulting acid to oxalyl chloride gives the corresponding acid chloride 27. Acylation of commercially available 4-nitroaniline (28) with the acid chloride 27 is followed by subsequent cyclization to the morpholinone 13-(6,6-$d_2$) upon treatment with potassium carbonate using the method described by Mederski, W W K R et al., Bioorg Med Chem Lett 2004, 14:5817-5822. The use of 4-(4-nitrophenyl)-6,6-$d_2$-morpholin-3-one as reagent 13 in Scheme 1 produces a compound of Formula I, wherein $X^{1a}$, $X^{1b}$, $X^{3a}$ and $X^{3b}$ are simultaneously hydrogen, and $X^{2a}$ and $X^{2b}$ are simultaneously deuterium.

Scheme 5. Synthesis of 4-(4-nitrophenyl)-2,2-$d_2$-morpholin-3-one.

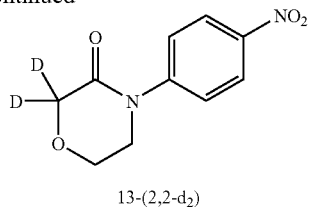

13-(2,2-d$_2$)

Scheme 5 shows a route for making 4-(4-nitrophenyl)-2,2-d$_2$-morpholin-3-one 13-(2,2-d$_2$). Treatment of commercially available d$_4$-acetic acid (29) with thionyl chloride and N-chlorosuccinimide (NCS), followed by dilution with methanol using the protocol described by Baldwin, J E-et al., J Am Chem Soc 1992, 114:9401-9408 affords methyl chloroacetate-2,2-d$_2$ 30. Treatment of the dideutero-chloroacetate 30 with 2-chloroethanol in the presence of sodium hydride according to the procedure described by Maruyama, T et al., Bioorg Med Chem 2002, 10:975-988 affords the dideuterated methylester 31. Saponification of the methyl ester 31 with sodium deuteroxide solution and exposure of the resulting acid to oxalyl chloride gives the corresponding acid chloride 32. Acylation of commercially available 4-nitroaniline (33) with the 2,2-d$_2$-(2-chloro-ethoxy)acetyl chloride 32 is followed by subsequent cyclization to the morpholinone 13-(2,2-d$_2$) upon treatment with potassium carbonate using the method described by Mederski, W W K R et al., Bioorg Med Chem Lett 2004, 14:5817-5822. The use of 4-(4-nitrophenyl)-2,2-d$_2$-morpholin-3-one as reagent 13 in Scheme 1 produces a compound of Formula I, wherein X$^{2a}$, X$^{2b}$, X$^{3a}$ and X$^{3b}$ are simultaneously hydrogen, and X$^{1a}$ and X$^{1b}$ are simultaneously deuterium.

Compounds of formula I wherein Y$^{1a}$ and Y$^{1b}$ are simultaneously deuterium are synthesized by using commercially available

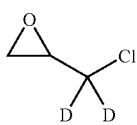

as reagent 15 in Scheme 1.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., R$^1$, R$^2$, R$^3$, etc.) or not. The suitability of a chemical group in a compound structure for use in the synthesis of another compound is within the knowledge of one of ordinary skill in the art. Additional methods of synthesizing compounds of Formula I and their synthetic precursors, including those within routes not explicitly shown in schemes herein, are within the means of chemists of ordinary skill in the art. Methods for optimizing reaction conditions and, if necessary, minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the U.S. Patent and Trademark Office text database.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formula I (e.g., including any of the formulae herein), or a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No.

7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the patient therapeutics may be local, so as to be administered at the site of interest. Various techniques can be used for providing the patient compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as rivaroxaban. Such agents indicated as being useful in combination with rivaroxaban, include but are not limited to, those described in WO 2003000256, and WO 2007039134.

Preferably, the second therapeutic agent is an agent useful in the treatment or prevention of a disease or condition selected from pulmonary embolism, stroke, thromboembolism, deep venous thrombosis, thrombosis, acute coronary syndrome, myocardial infarction, disorders of coagulation, and microangiopathy and associated disorders such as thrombocytopenic purpura.

In one embodiment, the second therapeutic agent is aspirin.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 0.025 to 300 mg per treatment. In more specific embodiments the range is from about 0.25 to 150 mg or 0.5 to 60 mg or most specifically from about 2.5 to 30 mg per treatment. Treatment typically is administered from about one to two times per day.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for rivaroxaban.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting the activity of coagulation factor Xa in a cell, comprising contacting a cell with one or more compounds of Formula I herein.

According to another embodiment, the invention provides a method of treating a disease that is beneficially treated by rivaroxaban in a patient in need thereof comprising the step of administering to said patient an effective amount of a compound or a composition of this invention. Such diseases are well known in the art and are disclosed in, but not limited to the following patents and published applications: WO 2001047919, WO 2003000256, WO 2007042146, WO 2007039122. Such diseases include, but are not limited to, pulmonary embolism, stroke, thromboembolism, deep venous thrombosis, thrombosis, myocardial infarction, acute coronary syndrome, disorders of coagulation, and microangiopathy and associated disorders such as thrombocytopenic purpura.

In one particular embodiment, the method of this invention is used to treat a disease or condition selected from pulmonary embolism, stroke, thromboembolism, deep venous thrombosis, thrombosis, myocardial infarction, and acute coronary syndrome in a patient in need thereof.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with rivaroxaban. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I and aspirin for treatment of acute coronary syndrome.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I for use in the treatment or prevention in a patient of a disease, disorder or symptom thereof delineated herein.

Diagnostic Methods and Kits

The compounds and compositions of this invention are also useful as reagents in methods for determining the concentration of rivaroxaban in solution or biological sample such as plasma, examining the metabolism of rivaroxaban and other analytical studies.

According to one embodiment, the invention provides a method of determining the concentration, in a solution or a biological sample, of rivaroxaban, comprising the steps of:
a) adding a known concentration of a compound of Formula I to the solution of biological sample;
b) subjecting the solution or biological sample to a measuring device that distinguishes rivaroxaban from a compound of Formula I;
c) calibrating the measuring device to correlate the detected quantity of the compound of Formula I with the known concentration of the compound of Formula I added to the biological sample or solution; and
d) measuring the quantity of rivaroxaban in the biological sample with said calibrated measuring device; and
e) determining the concentration of rivaroxaban in the solution of sample using the correlation between detected quantity and concentration obtained for a compound of Formula I.

Measuring devices that can distinguish rivaroxaban from the corresponding compound of Formula I include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the invention provides a method of evaluating the metabolic stability of a compound of Formula I in a patient following administration of the compound of Formula I. This method comprises the steps of obtaining a serum, urine or feces sample from the patient at a period of time following the administration of the compound of Formula I to the subject; and comparing the amount of the compound of Formula I with the metabolic products of the compound of Formula I in the serum, urine or feces sample.

The present invention also provides kits for use to treat pulmonary embolism, stroke, thromboembolism, deep venous thrombosis, thrombosis, myocardial infarction, and acute coronary syndrome. These kits comprise (a) a pharmaceutical composition comprising a compound of Formula I or a salt thereof, wherein said pharmaceutical composition is in a container; and (b) instructions describing a method of using the pharmaceutical composition to treat pulmonary embolism, stroke, thromboembolism, deep venous thrombosis, thrombosis, and acute coronary syndrome.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXPERIMENTAL

Example 1

Synthesis of 3,3,5,5-$d_4$-Morpholine (11a)

Intermediate 11a, was prepared as outlined in Scheme 6, below. Details of the synthesis are set forth below.

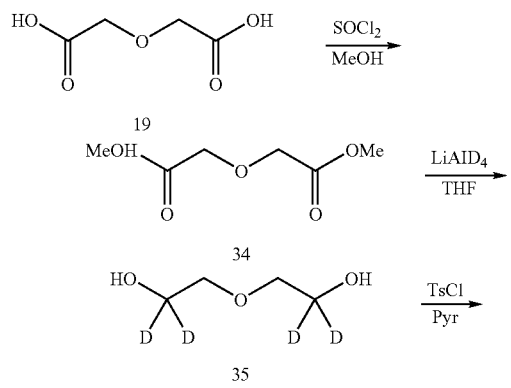

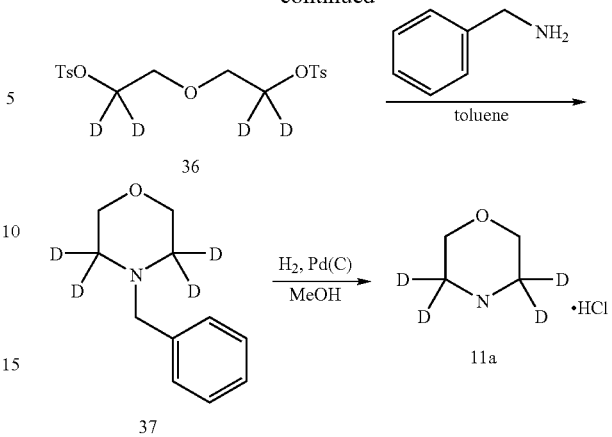

Synthesis of dimethyl 2,2'-oxydiacetate (34). A solution of diglycolic acid 19 (17.40 g, 129.76 mmol) in 100 mL of anhydrous methanol was stirred under a nitrogen atmosphere then cooled to 0° C. Thionyl chloride (21.72 mL, 35.51 g, 2.3 eq) was added dropwise over 10 minutes (min). The resulting mixture was allowed to warm to room temperature (rt) and was stirred overnight. The solvent was removed in vacuo and the resultant oil was dried under high vacuum to obtain 21.1 g (100%) of 34 as a crystalline, white solid.

Synthesis of 2,2'-oxybis(1,1-$d_2$-ethanol) (35). To a solution of LiAlD$_4$ (40.0 g, 0.953 mol, 2.3 eq)(Cambridge Isotope, 98 atom % D) in anhydrous THF (700 mL) at 0° C. under a nitrogen atmosphere was added 34 (67.2 g, 0.414 mol, 1.0 eq) in 800 mL THF dropwise over 2 hours (h). The reaction mixture was stirred under reflux conditions for 2 h then was cooled to 0° C. To this mixture was added 40 mL water, 40 mL of 15% aqueous NaOH, then 40 mL of water portionwise with stirring. After 30 min, the solid was removed by filtration and rinsed with THF (500 mL). The filtrate was concentrated in vacuo to yield 29.1 g (64%) of 35 as a yellow oil.

Synthesis of 2,2'-oxybis(1,1-$d_2$-ethane-2,1-diyl)bis(4-methylbenzenesulfonate) (36). To a solution of 35 (29.1 g, 0.264 mol) in pyridine (500 mL) at 0° C. was added p-toluenesulfonyl chloride (115.9 g, 0.608 mol, 2.3 eq) portionwise over 10 min. The reaction mixture was stirred for 1.5 h at 0° C., and then was poured into 600 mL brine and stirred for 10 min. The solid was collected by filtration, rinsed with water, then dried in vacuo to obtain 96.4 g (87%) of 36 as a white solid.

Synthesis of 4-benzyl-3,3,5,5-$d_4$-morpholine (37). To the bis-sulfonate 36 (96.4 g, 0.230 mol) in 1.5 L anhydrous toluene under an atmosphere of nitrogen was added benzylamine (252 mL, 246.8 g, 2.303 mmol, 10 eq). The mixture was stirred at reflux for 18 h and then was allowed to cool to rt. The solvent was removed under reduced pressure and excess benzylamine was removed by vacuum distillation to afford 32.12 g of the mother liquor containing 37, which was used directly in the next step without further purification.

Synthesis of 3,3,5,5-$d_4$-morpholine (11a)—To a solution of 37 (32.12 g, obtained from the previous step) in methanol (150 mL) was added 20% Pd(OH)$_2$ (4 g). The mixture was shaken under an atmosphere of hydrogen at 30 psi for 2 days, then was filtered over Celite and the solid was rinsed with methanol. The filtrate was concentrated in vacuo, then the resultant oil was dissolved in 300 mL anhydrous ether and treated with 44 mL of 4N HCl to form a white precipitate. The ether was decanted and the solid rinsed with ether again. The solvent was decanted and the solid was dried under vacuum to yield 18.54 g (64% over 2 steps) of 11a as a white solid.

Example 2
Synthesis of (S)-5-Chloro-N-((2-oxo-3-(4-(3-oxo-2,2,5,5,6,6-$d_6$-morpholino)phenyl)oxazolidin-5-yl)methyl)thiophene-2-carboxamide (101)
Compound 101 was prepared as outlined in Scheme 1 above, and Scheme 7 below. Details of the synthesis are as follows.
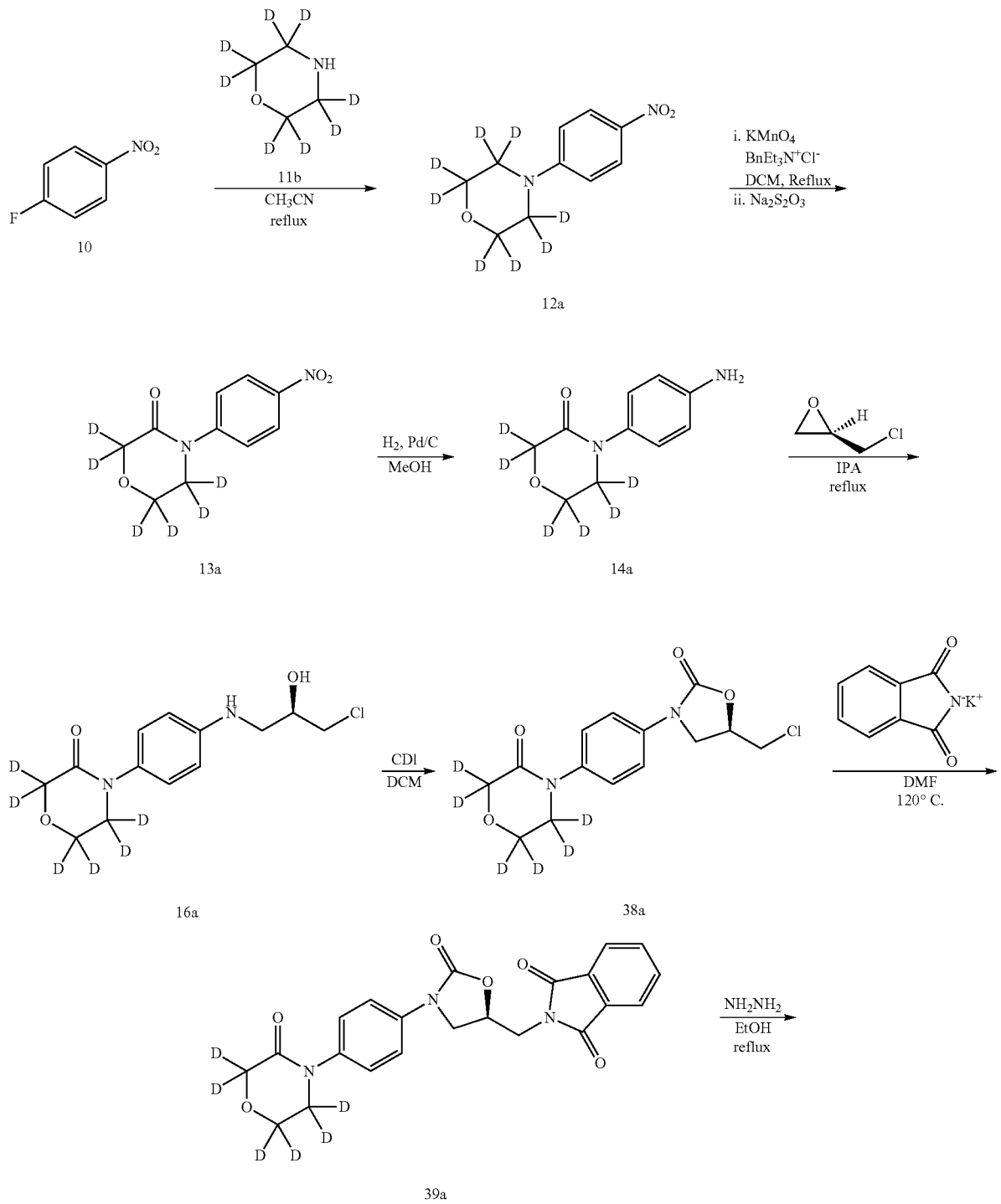
Scheme 7. Synthesis of 101.

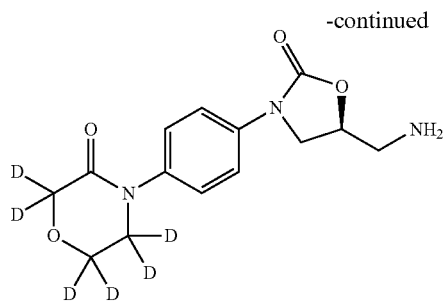

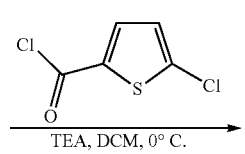

18a

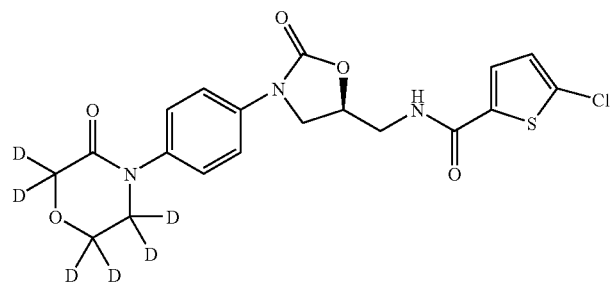

101

Synthesis of 4-(4-nitrophenyl)morpholine-d$_8$ (12a). To a stirred solution of 1-fluoro-4-nitrobenzene 10 (13.47 g, 95.49 mmol) in 100 mL acetonitrile under a nitrogen atmosphere was added morpholine-d$_8$ 11b (10.0 g, 105.04 mmol, 1.1 eq) (Cambridge Isotopes, 98 atom % D) followed by triethylamine (14.64 mL, 10.63 g, 105.04 mmol, 1.1 eq). The mixture was stirred at reflux for 16 h, then cooled to rt. The mixture was then poured into 400 mL water and extracted with ethyl acetate (2×400 mL). The combined organic layers were washed with brine (300 mL), dried over sodium sulfate, concentrated in vacuo, then dried under vacuum to obtain 19.1 g (92%) of 12a as yellow solid.

Synthesis of 4-(4-nitrophenyl)-2,2,5,5,6,6-d$_6$-morpholin-3-one (13a). To a solution of 12a (14.00 g, 64.74 mmol) in 500 mL dichloromethane was added potassium permanganate (30.70 g, 194.20 mmol, 3 eq) and benzyltriethylammonium chloride (44.20 g, 194.20 mmol, 3 eq) with stirring. The reaction mixture was allowed to stir at reflux for 15 h then was cooled to rt and washed with 350 mL of 10% sodium thiosulfate in water. The aqueous layer was extracted with 400 mL dichloromethane and the combined organic layers were washed with 300 mL brine then dried over sodium sulfate and concentrated in vacuo. The resultant dark oil was purified by silica gel chromatography eluting with methanol in dichloromethane (0-10% gradient) to yield 5.76 g (39%) of 13a as a yellow-orange solid. The fractions containing starting material and traces of product (~7 g total) were re-subjected to the oxidation conditions.

Synthesis of 4-(4-aminophenyl)-2,2,5,5,6,6-d$_6$-morpholin-3-one (14a). To a stirred solution of 13a (10.41 g, 45.60 mmol) in 300 mL methanol under a nitrogen atmosphere was added 2.0 g of 20% Pd(C)/50% H$_2$O. The mixture was placed under hydrogen at 1 atmosphere for 30 minutes then was filtered through Celite. The solid was rinsed with methanol and the filtrate was concentrated in vacuo then triturated with methanol to remove impurities. The solid was dried under vacuum to obtain 6.60 g (73%) of 14a as a dark brown solid. $^1$H-NMR (300 MHz, DMSO-d$_6$): δ 5.13 (s, 2H), 6.54 (d, J=8.8, 1H), 6.95 (d, J=8.8, 1H). $^{13}$C-NMR (75 MHz, DMSO-d$_6$): δ 114.34, 127.11, 130.90, 148.06, 166.48. HPLC (method: Zorbax 4.6×50 mm SB-Aq 3.5 μm column-gradient method 2 to 98% ACN+0.1% formic acid in 6.0 min; 0.63 mL/min; Wavelength: 254 nm): retention time: 2.17 min; 98.0% purity. MS (M+H): 199.1.

Elemental Analysis (C$_{10}$H$_6$D$_6$N$_2$O$_2$): Calculated: C=60.59, H=6.10, N=14.13. Found: C=60.34, H=6.09, N=13.97.

Synthesis of (R)-4-(4-(3-chloro-2-hydroxypropylamino) phenyl)-2,2,5,5,6,6-d$_6$-morpholin-3-one (16a). To a solution of 14a (7.00 g, 35.31 mmol) in 40 mL isopropanol was added (R)-epichlorohydrin (4.14 mL, 4.90 g, 52.96 mmol, 1.5 eq). The mixture was stirred under an atmosphere of nitrogen at reflux for 16 h. The solvent was then removed under vacuum and the dark solid was used directly in the next step.

Synthesis of (R)-4-(4-(5-(chloromethyl)-2-oxooxazolidin-3-yl)phenyl)-2,2,5,5,6,6-d$_6$-morpholin-3-one (38a). A solution of 16a (from the previous step) in 100 mL dichloromethane was placed under an atmosphere of nitrogen and carbonyldiimidazole (17.18 g, 105.93 mmol, 3 eq) was added with stirring. The mixture was allowed to stir at rt for 3 h then was concentrated in vacuo. The resultant oil was purified via chromatography using silica gel eluted with methanol in dichloromethane (0-10% gradient). The fractions containing 38a were combined and concentrated in vacuo, then triturated with methanol for 30 minutes at rt. Methanol was decanted and the remaining solid was dried under vacuum at 50° C. overnight to yield 3.27 g (29% over 2 steps) of 38a as a beige solid.

Synthesis of (S)-2-((2-oxo-3-(4-(3-oxo-2,2,5,5,6,6-d$_6$-morpholino)phenyl)oxazolidin-5-yl)methyl)isoindoline-1,3-dione (39a). To a solution of 38a (3.20 g, 10.10 mmol) in 20 mL anhydrous DMF was added potassium phthalimide (3.74 g, 20.21 mmol, 2 eq). The mixture was stirred under an atmosphere of nitrogen at 120° C. for 2 h, then at rt overnight (14 h). The mixture was then heated to 125° C. and stirred for 4 hours before additional potassium phthalimide (1.87 g, 1 eq) was added. Stirring was continued for an additional 2 h at 125° C., the mixture was cooled to rt, then was poured into 300 mL methanol. After 30 minutes a white precipitate formed. The resultant solid was filtered and dried under vacuum to obtain 2.39 g (55%) of 39a as a beige solid.

(S)-4-(4-(5-(aminomethyl)-2-oxooxazolidin-3-yl)phenyl)-2,2,5,5,6,6-$d_6$-morpholin-3-one (18a). To a solution of 39a (2.36 μg, 5.52 mmol) in 50 mL ethanol was added hydrazine (0.69 g, 13.81 mmol, 2.5 eq). The mixture was stirred at reflux for 4.5 h, and then allowed to cool to rt. The newly formed precipitate was filtered and rinsed with ethanol. The filtrate was concentrated under vacuum to obtain 900 mg of 18a as a white solid which contained traces of phthalazine by-product. The material was used directly in the next step without further purification.

Synthesis of (S)-5-chloro-N-((2-oxo-3-(4-(3-oxo-2,2,5,5,6,6-$d_6$-morpholino)phenyl)oxazolidin-5-yl)methyl)thiophene-2-carboxamide (101). To a solution of 5-chlorothiophene-2-carbonic acid (738 mg, 4.54 mmol, 1.5 eq) in 15 mL dichloromethane at 0° C. was added dropwise thionyl chloride (540 mg, 0.33 mL, 4.54 mmol, 1.5 eq). Five drops of DMF were added to catalyze the reaction. The reaction mixture was analyzed periodically using an aliquot quenched with methylamine. After 2 h an additional 0.33 mL of thionyl chloride were added, stirring was continued for 2 h and a third portion of thionyl chloride (0.38 mL) was added. The mixture was stirred for 1 h at rt then solvent was removed in vacuo. The resultant oil was dissolved in 10 mL dichloromethane and this solution was added to a solution of 18a (900 mg, 3.03 mmol, 1 eq) and triethylamine (1.27 mL, 919 mg, 9.08 mmol, 3 eq) in 15 mL dichloromethane at 0° C. The mixture was allowed to warm to rt overnight (16 h) then was poured into 120 mL of saturated aqueous sodium bicarbonate and extracted with ethyl acetate (2×200 mL). The combined organic layers were washed with brine (150 mL), then dried over sodium sulfate. The organic layer was concentrated in vacuo and the resultant solid was recrystallized from methanol to yield 740 mg (56%) of compound 101 as a white solid. The mother liquor was concentrated and recrystallization from methanol yielded 130 mg (10%) of a second crop of 101. $^1$H-NMR (300 MHz, DMSO-$d_6$): δ 3.60 (t, J=5.6, 2H), 3.84 (dd, $J_1$=9.3, $J_2$=6.4, 1H), 4.18 (t, J=9.1, 1H), 4.79-4.88 (m, 1H), 7.19 (d, J=4.1, 1H), 7.41 (d, J=8.8, 2H), 7.55 (d, J=8.8, 2H), 7.69 (d, J=4.1, 1H), 8.99 (t, J=5.8, 1H). $^{13}$C-NMR (75 MHz, DMSO-$d_6$): δ 42.90, 48.11, 72.02, 119.01, 126.61, 128.88, 129.14, 133.96, 137.15, 137.73, 139.16, 154.80, 161.49, 166.70. HPLC (method: 20 mm C18-RP column-gradient method 2 to 95% ACN+0.1% formic acid in 3.3 min with 1.7 min hold at 95% ACN; Wavelength: 254 nm): retention time: 2.93 min; 98.2% purity. MS (M+H): 442.2. Elemental Analysis ($C_{19}H_{12}D_6ClN_3O_5S$):
Calculated: C=51.64, H=4.11, N=9.51, Cl=8.02, S=7.26.
Found: C=51.74, H=3.76, N=9.45, Cl=8.29, S=7.35.

Example 3

Synthesis of (S)-5-chloro-N-((2-oxo-3-(4-(3-oxo-5,5-$d_2$-morpholino)phenyl)oxazolidin-5-yl)methyl)thiophene-2-carboxamide (114)

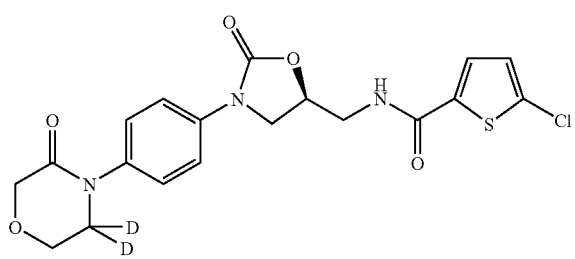

114

Compound 114 was prepared as outlined in Scheme 7 above with the exception that 3,3,5,5-$d_4$-morpholine (11a) was used in place of morpholine-$d_8$ (11b). Details of the synthesis are as follows.

Synthesis of 4-(4-nitrophenyl)-3,3,5,5-$d_4$-morpholine (12b)

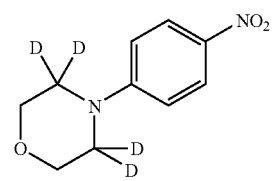

12b

To a stirred solution of 1-fluoro-4-nitrobenzene 10 (12.16 g, 86.17 mmol, 1.1 eq) in 100 mL acetonitrile under a nitrogen atmosphere was added 11a (10.0 g, 78.34 mmol) followed by triethylamine (32.76 mL, 23.78 g, 235.01 mmol, 3.0 eq). The mixture was stirred at reflux for 16 h, then cooled to rt. The mixture was then poured into 400 mL water and extracted with ethyl acetate (2×700 mL). The combined organic layers were washed with brine (300 mL), dried over sodium sulfate, concentrated in vacuo. The resultant oil was purified via chromatography using silica gel eluted with methanol in dichloromethane (0-10% gradient) to yield 14.94 g (90%) of 12b as yellow solid.

Synthesis of 4-(4-nitrophenyl)-5,5-$d_2$-morpholin-3-one (13b)

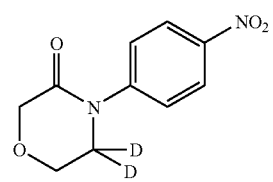

13b

To a stirred solution of 12b (16.20 g, 76.32 mmol) in 700 mL dichloromethane was added potassium permanganate (36.18 g, 228.96 mmol, 3 eq) and benzyltriethylammonium chloride (52.15 g, 228.96 mmol, 3 eq). The reaction mixture was allowed to stir at reflux for 24 h and another 36 g of potassium permanganate was added. After an additional 24 h the reaction was cooled to rt and washed with 350 mL of 10% sodium thiosulfate in water. The aqueous layer was extracted with dichloromethane (2×400 mL) and the combined organic layers were washed with 300 mL brine then dried over sodium sulfate and concentrated in vacuo. The resultant dark oil was purified by silica gel chromatography eluting with methanol in dichloromethane (0-10% gradient) to yield 4.56 g (27%) of 13b as a yellow-orange solid. The fractions containing starting material and traces of product (~7 g total) were re-subjected to the oxidation conditions listed above.

Synthesis of 4-(4-aminophenyl)-5,5-d$_2$-morpholin-3-one (14b)

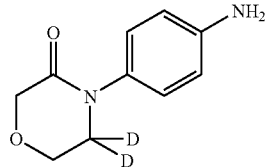

To a stirred solution of 13b (4.50 g, 20.07 mmol) in 100 mL methanol under a nitrogen atmosphere was added 1.0 g of 20% Pd(C)/50% H$_2$O. The mixture was placed under hydrogen at 1 atmosphere for 2 h then was filtered through Celite. The solid was rinsed with methanol and the filtrate was concentrated in vacuo to yield 3.57 g (91%) of 14b as a dark brown solid.

Synthesis of (R)-4-(4-(3-chloro-2-hydroxypropylamino)phenyl)-5,5-d$_6$-morpholin-3-one (16b)

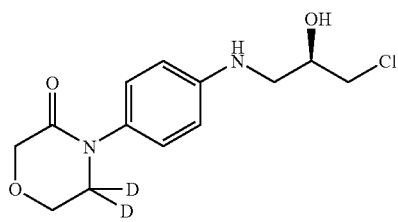

To a solution of 14b (3.41 g, 17.56 mmol) in 20 mL isopropanol was added (R)-epichlorohydrin (2.06 mL, 2.44 g, 26.33 mmol, 1.5 eq). The mixture was stirred under an atmosphere of nitrogen at reflux for 16 h. The solvent was then removed under vacuum and the dark solid was used directly in the next step.

Synthesis of (R)-4-(4-(5-(chloromethyl)-2-oxooxazolidin-3-yl)phenyl)-5,5-d$_6$-morpholin-3-one (38b)

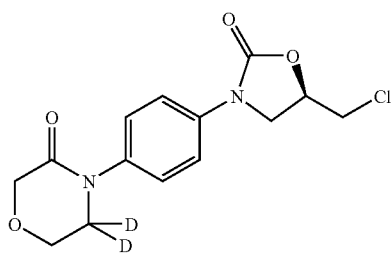

A solution of 16b (from the previous step) in 50 mL dichloromethane was placed under an atmosphere of nitrogen and carbonyldiimidazole (8.56 g, 52.67 mmol, 3 eq) was added with stirring. The mixture was allowed to stir at rt for 3 h then was concentrated in vacuo. The resulting oil was purified via chromatography using silica gel eluted with methanol in dichloromethane (0-10% gradient) to yield 1.62 g (30% over 2 steps) of 38b as a beige solid.

Synthesis of (S)-2-((2-oxo-3-(4-(3-oxo-5,5-d$_2$-morpholino)phenyl)oxazolidin-5-yl)methyl)isoindoline-1,3-dione (39b)

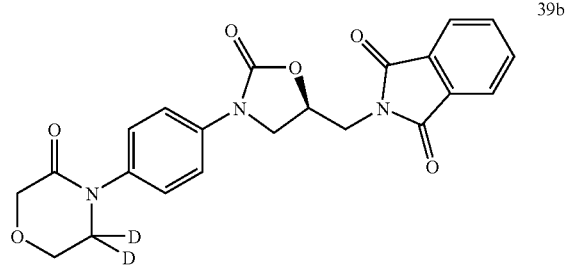

To a solution of 38b (1.60 g, 5.12 mmol) in 10 mL anhydrous DMF was added potassium phthalimide (2.81 g, 15.35 mmol, 3 eq). The mixture was stirred under an atmosphere of nitrogen at 120° C. for 3.5 h, then was cooled to rt. The solvent was removed in vacuo and the remaining solid was triturated with methanol, filtered, and dried under vacuum to obtain 1.22 g (56%) of 39b as a beige solid.

Synthesis of (S)-4-(4-(5-(aminomethyl)-2-oxooxazolidin-3-yl)phenyl)-5,5-d$_6$-morpholin-3-one (18b)

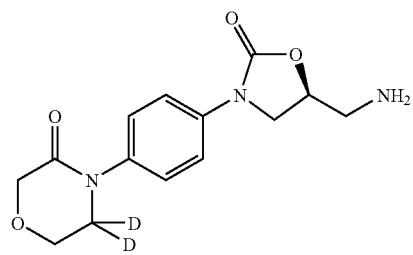

To a solution of 39b (1.57 g, 3.75 mmol) in 40 mL ethanol was added hydrazine (0.47 g, 9.39 mmol, 2.5 eq). The mixture was stirred at reflux for 2 h, and then allowed to cool to rt. The newly formed precipitate was filtered and rinsed with ethanol. The filtrate was concentrated under vacuum to obtain 758 mg of 18b as a white solid which contained traces of phthalazine by-product. The material was used directly in the next step without further purification.

Synthesis of (S)-5-chloro-N-((2-oxo-3-(4-(3-oxo-5,5-d$_2$-morpholino)phenyl)oxazolidin-5-yl)methyl)thiophene-2-carboxamide (114). To a solution of 5-chlorothiophene-2-carbonic acid (628 mg, 3.86 mmol, 1.5 eq) in 15 mL dichloromethane at 0° C. was added dropwise thionyl chloride (1.53 g, 0.94 mL, 12.88 mmol, 5 eq). Five drops of DMF were added to catalyze the reaction. The reaction mixture was analyzed periodically using an aliquot quenched with methylamine. After 2 h an additional 2.16 mL of thionyl chloride were added and stirring was continued for 2 h. Solvent was removed in vacuo, the resultant oil was dissolved in 10 mL dichloromethane and this solution was added to a solution of 18b (758 mg, 2.58 mmol, 1 eq) and triethylamine (1.08 mL, 782 mg, 7.73 mmol, 3 eq) in 10 mL dichloromethane at 0° C.

The mixture was allowed to warm to rt overnight (16 h) then was poured into 120 mL of saturated aqueous sodium bicarbonate and extracted with ethyl acetate (2×200 mL). The combined organic layers were washed with brine (150 mL), then dried over sodium sulfate. The organic layer was concentrated in vacuo and the resultant solid was recrystallized from methanol to yield 215 mg (13%) of compound 114 as a white solid. The mother liquor was concentrated and further recrystallization from methanol yielded 110 mg of a second crop of 114 which contained major impurities. $^1$H-NMR (300 MHz, DMSO-$d_6$): δ 3.60 (t, J=5.4, 2H), 3.84 (dd, $J_1$=9.2, $J_2$=5.8, 1H), 3.95 (s, 2H), 4.15-4.21 (m, 3H), 4.79-4.88 (m, 1H), 7.19 (d, J=4.2, 1H), 7.40 (d, J=8.3, 2H), 7.55 (d, J=8.3, 2H), 7.68 (d, J=4.2, 1H), 8.97 (t, J=5.8, 1H). $^{13}$C-NMR (75 MHz, DMSO-$d_6$): δ 42.90, 48.11, 64.02, 68.40, 72.00, 119.00, 126.58, 128.84, 129.12, 133.93, 137.14, 137.72, 139.13, 154.77, 161.47, 166.64. HPLC (method: Waters Atlantis T3 2.1×50 mm 3 μm C18 column-gradient method 5 to 95% ACN+0.1% formic acid in 14 min, hold at 95% ACN for 4 min; 1.0 mL/min; Wavelength: 254 nm): retention time: 5.03 min; 99.4% purity. MS (M+H): 438.0. Elemental Analysis ($C_{19}H_{16}D_2ClN_3O_5S$): Calculated: C=52.12, H=4.14, N=9.60, Cl=8.10, S=7.32. Found: C=52.02, H=4.01, N=9.47, Cl=7.92, S=7.10.

Example 4

Evaluation Of Metabolic Stability in Microsomes

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay: The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures: Human liver microsomes are obtained from a commercial source (e.g., Absorption Systems L.P. (Exton, Pa.)). The incubation mixtures are prepared as follows:

| Reaction Mixture Composition | |
|---|---|
| Liver Microsomes | 1.0 mg/mL |
| NADPH | 1 mM |
| Potassium Phosphate, pH 7.4 | 100 mM |
| Magnesium Chloride | 10 mM |
| Test Compound | 1 μM. |

Incubation of Test Compounds with Liver Microsomes: The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 μM. An aliquot of the reaction mixture is prepared as a blank control, by the addition of plain organic solvent (not the test compound). The reaction is initiated by the addition of cofactors (not into the negative controls), and then incubated in a shaking water bath at 37° C. Aliquots (200 μL) are withdrawn in triplicate at multiple time points (e.g., 0, 15, 30, 60, and 120 minutes) and combined with 800 μL of ice-cold 50/50 acetonitrile/d$H_2$O to terminate the reaction. The positive controls, testosterone and propranolol, as well as rivaroxaban, are each run simultaneously with the test compounds in separate reactions.

All samples are analyzed using LC-MS (or MS/MS). An LC-MRM-MS/MS method is used for metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

SUPERSOMES™ Assay. Various human cytochrome P450-specific SUPERSOMES™ are purchased from Gentest (Woburn, Mass., U.S.A.). A 1.0 mL reaction mixture containing 25 pmole of SUPERSOMES™, 2.0 mM NADPH, 3.0 mM MgCl, and 1 μM of a test compound in 100 mM potassium phosphate buffer (pH 7.4) is incubated at 37° C. in triplicate. Positive controls contain 1 μM of rivaroxaban instead of a test compound. Negative controls used Control Insect Cell Cytosol (insect cell microsomes that lacked any human metabolic enzyme) purchased from GenTest (Woburn, Mass., U.S.A.). Aliquots (50 μL) are removed from each sample and placed in wells of a multi-well plate at various time points (e.g., 0, 2, 5, 7, 12, 20, and 30 minutes) and to each aliquot is added 50 μL of ice cold acetonitrile with 3 μM haloperidol as an internal standard to stop the reaction.

Plates containing the removed aliquots are placed in −20° C. freezer for 15 minutes to cool. After cooling, 100 μL of deionized water is added to all wells in the plate. Plates are then spun in the centrifuge for 10 minutes at 3000 rpm. A portion of the supernatant (100 μL) is then removed, placed in a new plate and analyzed using Mass Spectrometry.

Example 6

Evaluation of Pharmacokinetics of Compound 101 in Male Sprague Dawley Rats Following Oral Administration Separate solutions of rivaroxaban and Compound 101 were prepared using 20% ethanol, 60% PEG400, 20% dimethyl isosorbide to provide a concentration of 10 mg/mL. The concentration of each solution was confirmed by HPLC prior to further use. A combination dose of rivaroxaban and Compound 101 was prepared by mixing the two solutions in a 1.09:1 ratio to yield a final concentration of 5.45 mg/mL of rivaroxaban and 5 mg/mL for Compound 101.

Two male Sprague Dawley rats were dosed by oral gavage with the combination dose containing rivaroxaban (5.45 mg/kg) and compound 101 (5 mg/kg). Blood samples (approximately 0.25 mL) were collected retro-orbitally following oral administration at 0 minutes (min) (pre-dose), 5 min, 15 min, 30 min, hr, 1.5 hr, 2 hr, 4 hr, 6 hr, 8 hr, 10 hr and 24 hr post-dose. Blood samples were stored on ice and centrifuged within 15 minutes of collection to harvest plasma. The plasma was decanted immediately and frozen at −20° C. until analysis.

Analyses of plasma samples were performed using a high performance liquid chromatography/mass spectrometry (HPLC/MS/MS) method. The LC system comprised an Agilent (Agilent Technologies Inc. U.S.A.) liquid chromatograph equipped with an isocratic pump (1100 series), an autosampler (1100 series) and a degasser (1100 series). Mass spectrometric analysis was performed using an API3000 (triple-quadrupole) instrument from AB Inc (Canada) with an ESI interface. The data acquisition and control system were created using Analyst 1.4 software from ABI Inc. Data for rivaroxaban was corrected by multiplying by a factor of 0.91 to compensate for the 9% increased amount administered as compared to Compound 101.

The results are depicted in the table below.

TABLE 2

Calculated Pharmacokinetic Values of Compound 101 and Rivaroxaban After Oral Co-Dosing in Rats

| Compound | $AUC_\infty$ (ng-h/ml) | $C_{max}$ (ng/ml) |
|---|---|---|
| Rivaroxaban | 2926.95 | 842 |
| Compound 101 | 3424.33 | 962 |

The data above shows that Compound 101 demonstrated a greater than 16% increase in AUC and a greater than 14% increase in $C_{max}$ as compared to rivaroxaban.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of Formula I:

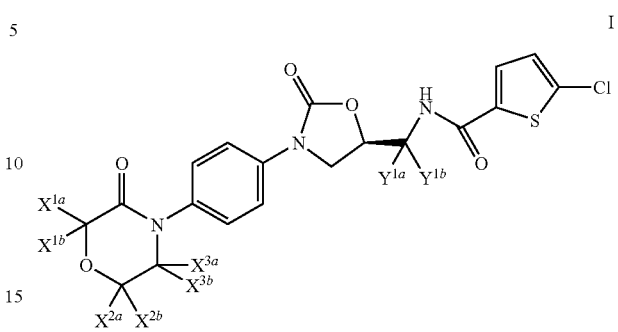

or a pharmaceutically acceptable salt thereof, wherein:
each of $X^{1a}$, $X^{1b}$, $X^{2a}$, $X^{2b}$, $X^{3a}$, and $X^{3b}$ is deuterium; and
$Y^{1a}$, and $Y^{1b}$ are the same and are selected from hydrogen and deuterium.

2. The compound of claim 1, or a pharmaceutically acceptable salt thereof, wherein $Y^{1a}$ and $Y^{1b}$ are simultaneously hydrogen.

3. The compound of claim 1 or 2, or a pharmaceutically acceptable salt thereof, wherein any atom not designated as deuterium is present at its natural isotopic abundance.

4. A pyrogen-free composition comprising a compound of claim 1,
or a pharmaceutically acceptable salt thereof,
and a pharmaceutically acceptable carrier.

5. The pharmaceutical composition of claim 4, further comprising a therapeutic agent useful in the treatment of a disease or condition selected from pulmonary embolism, stroke, thromboembolism, deep venous thrombosis, thrombosis, myocardial infarction, acute coronary syndrome, disorders of coagulation, microangiopathy and thrombocytopenic purpura.

6. The pharmaceutical composition of claim 5, wherein the therapeutic agent is aspirin.

* * * * *